United States Patent [19]
Keil et al.

[11] Patent Number: 5,300,652
[45] Date of Patent: Apr. 5, 1994

[54] PREPARATION OF MONOCLINIC METAZACHLOR

[75] Inventors: Michael Keil, Freinsheim; Bjoern Girgensohn, Mannheim; Gotthard Synnatschke, Ludwigshafen; August Wigger, Neuhofen; Hans Ziegler, Mutterstadt; Walter Gueckel, Limburgerhof, all of Fed. Rep. of Germany

[73] Assignee: BASF Aktiengesellschaft, Ludwigshafen, Fed. Rep. of Germany

[21] Appl. No.: 47,290

[22] Filed: Apr. 19, 1993

Related U.S. Application Data

[60] Division of Ser. No. 920,815, Jul. 24, 1992, Pat. No. 5,250,503, which is a continuation of Ser. No. 551,778, Jul. 12, 1990, abandoned.

[30] Foreign Application Priority Data

Jul. 29, 1989 [DE] Fed. Rep. of Germany ....... 3925253

[51] Int. Cl.$^5$ ............................................ C07D 231/12
[52] U.S. Cl. .................................................. 548/375.1
[58] Field of Search ...................................... 548/375.1

[56] References Cited

U.S. PATENT DOCUMENTS

| 4,321,395 | 3/1982 | Eicken et al. | 548/375.1 |
| 4,593,104 | 6/1986 | Eicken et al. | 548/375.1 |

FOREIGN PATENT DOCUMENTS 1120043  3/1982  Canada .

Primary Examiner—Robert W. Ramsuer
Attorney, Agent, or Firm—Keil & Weinkauf

[57] ABSTRACT

Monoclinic 2-chloro-(2',6'-dimethyl-N-pyrazol-1-ylmethyl)-acetanilide of the formula I

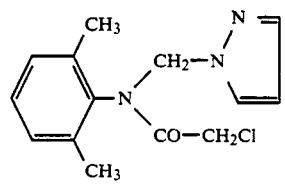

which melts at 76° C.

1 Claim, No Drawings

PREPARATION OF MONOCLINIC METAZACHLOR

This is a division of application Ser. No. 07/920,815, filed Jul. 24, 1992, now U.S. Pat. No. 5,250,503, which is a continuation of Ser. No. 07/551,778, filed Jul. 12, 1990, now abandoned.

The present invention relates to monoclinic 2-chloro-(2',6'-dimethyl-N-pyrazol-1-ylmethyl)-acetanilide of the formula I

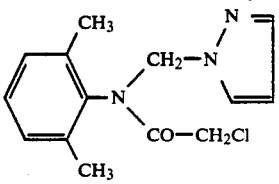

which melts at 76° C., and processes for the preparation of this modification, its use as a herbicide, and herbicides which contain this active ingredient.

The important herbicidal active ingredient 2-chloro-(2',6'-chloro-(2',6'-dimethyl-N-pyrazol-1-ylmethyl)-acetanilide I (common name: metazachlor) melts, as far as is known, in a range of 78–83° C. and crystallizes in a triclinic crystalline form. This crystalline form IA is obtained by the methods described in DE-A 2 648 008, DE-A 2 830 764 and EP-A 12216, by crystallization of I from a non-polar or slightly polar solvent, such as cyclohexane or toluene.

However, this known modification IA of metazachlor, which is commercially available in the form of concentrated aqueous suspensions, has the disadvantage that it frequently forms agglomerates.

The agents then cannot be sprayed uniformly, if at all.

In efforts aimed at remedying this deficiency, a monoclinic modification of I, which modification melts at 76° C., was found.

This monoclinic modification IB is obtained if water is added to an aqueous metazachlor solution containing sulfuric acid, at from 0° to 50° C., in the presence of a water-miscible polar inert organic solvent, and the resulting solid is isolated in a conventional manner after crystallization is complete.

In this process, the order in which the active ingredient solution, the organic solvent and the water are mixed with one another is unimportant for the crystallization.

Seeding with crystals of modification IB is not essential but generally proves advantageous.

Particular suitable protic polar inert solvents are alcohols, such as methanol, ethanol, isopropanol, n-propanol, 1-butanol, 2-butanol, isobutanol, tert-butanol, ethylene glycol, propylene glycol, propane-1,3-diol and butanediols, ketones, such as acetone and butan-2-one, ethers, such as tetrahydrofuran and 1,4-dioxane, amides, such as dimethylformamide and N-methylpyrrolidone, and dimethyl sulfoxide and diethylene glycol.

The seed crystals required for the preparation of metazachlor in modification IB in amounts of from 0.01 to 50% by weight can be obtained for the first time, for example, by recrystallization of metazachlor of modification IA from the abovementioned polar organic solvents.

In another possible method for the preparation of metazachlor of modification IB, from 0.01 to 50% by weight of seed crystals of modification IB are added to an aqueous suspension of metazachlor of modification IA at a pH of from 0 to 10, with or without the addition of one or more of the abovementioned water-soluble organic solvents, at from 0 to 45° C., and stirring is carried out at from 0.1 to 20 hours. Modification IA is transformed into modification IB.

This transformation also takes place in a similar manner when an aqueous suspension of modification IA is milled in the presence of the stated organic solvents with the addition of seed crystals of modification IB.

Characteristic physical data for distinguishing between the two modifications are summarized in the Table below.

TABLE

| Method of measurement | Unit | IA | IB |
|---|---|---|---|
| Differential thermal analysis | °C. | 79 | 76 |
| IR spectroscopy* | cm$^{-1}$ | 3160, 1300 | 1360, 780 |
| X-ray diffraction pattern (diffraction angle 2 $\theta$) | degrees | 8.2; 8.4 | 9.9; 12.3 |
| Solid-state $^{13}$C-NMR spectroscopy* (against adamantane) | $\delta$ in ppm | 62.5; 137.1 | 51.4; 139.1 |
| Modification from X-ray structural analysis | — | triclinic | monoclinic |
| Microscopy (crystal form) | — | amorphous | coffin-lid-shaped |

*Selected signals

The effect of the invention is as follows:

Formulated product containing metazachlor of the known modification IA changes during storage. The size of the suspended particles increases continuously; in the formulated product, this is evident in the formation of fragments right up to complete solidification of the previously liquid product, so that uniform application of the product is no longer ensured.

Formulated product containing metazachlor of modification IB does not have this undesirable behavior and can be applied satisfactorily even after prolonged storage.

During these investigations, a further metastable metazachlor modification IC which melts at 840C was found. This modification is obtained by heating metazachlor of modification IA to 84° C. and milling the melt formed.

On standing, the metazachlor modification IC, which has a half-life of about 5 days, is transformed into modification IB, which melts at 76° C.

The Examples which follow illustrate the novel process:

1. Precipitation of an acidic aqueous metazachlor solution with seeding with modification IB a) 1,250 ml of water and 22 ml of methanol are initially taken at 25° C. For seeding, 3.8 g of metazachlor of modification IB are added. 62.5 g of a 40% strength metazachlor solution in 60% strength sulfuric acid are then added slowly while stirring, stirring is continued for one hour and a further 562.5 g of the metazachlor solution are then added rapidly. After complete precipitation, the precipitate is isolated, washed with water and dried. 247 g of metazachlor of modification IB are obtained.

b) 7.6 g of methanol and 51 g of water are added to a solution of 63 g of metazachlor of modification IA in 90 g of 60% strength sulfuric acid, while stirring, at 40°C. After the addition of 3 g of metazachlor of modification IB, 133 ml of water are added in the course of two hours and then a further 113 ml of water are added rapidly. Stirring is continued for two hours and the product is filtered off under suction, washed with 200 ml of water and then dried. 62.3 g of metazachlor of modification IB are obtained.

2. Preparation of metazachlor of modification IB by transformation of the crystalline modification IA in aqueous suspension 1 g of modification IB is added to a suspension of 10 g of metazachlor of modification IA in 127 g of 15% strength sulfuric acid and 2 g of methanol, the mixture is stirred for 20 hours at 20° C. and the product is filtered off under suction and washed with 500 ml of water. Metazachlor of modification IB is obtained.

3. Preparation of metazachlor of modification IB by crystallization from methanolic aqueous solution A mixture of 2.2 l of methanol and 1,500 g of metazachlor of modification IA is converted into a solution at 50° C. The solution is slowly allowed to reach room temperature, and 5.2 l of water are slowly added to the partially crystallizing mixture. Filtration under suction and washing with 1 l of water give 1,485 g of metazachlor of modification IB.

We claim:

1. A process for the preparation of crystalline monoclinic-2-chloro-(2',6'-dimethyl-N-pyrazazol-1-ylmethyl)-acetanilide of the formula I

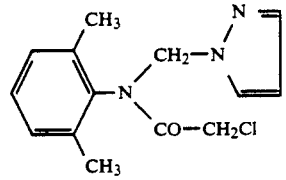

which melts at 76° C., which process comprises: mixing an aqueous solution containing sulfuric acid of modification 1B of the compound I with water and with a water-miscible polar inert organic solvent selected from the group consisting of an alcohol, a ketone, dimethyl sulfoxide and diethylene glycol at from 0° to 50° C. to precipitate the crystalline monoclinic modification 1A of the compound I from the aqueous solution, and thereafter isolating the crystalline product.

* * * * *

UNITED STATES PATENT AND TRADEMARK OFFICE
CERTIFICATE OF CORRECTION

PATENT NO. : 5,300,652
DATED : April 5, 1994
INVENTOR(S) : KEIL et al.

It is certified that error appears in the above-indentified patent and that said Letters Patent is hereby corrected as shown below:

Title page, item [57],
<u>IN THE ABSTRACT</u>, last line,

After "76°C." insert -- Processes for its preparation and herbicides.--

Signed and Sealed this

Ninth Day of August, 1994

Attest:

BRUCE LEHMAN

Attesting Officer

Commissioner of Patents and Trademarks